United States Patent [19]
Bathe et al.

[11] Patent Number: 5,732,694
[45] Date of Patent: Mar. 31, 1998

[54] SYSTEM FOR CORRECTING $NO_2$ MONITOR

[75] Inventors: Duncan P. L. Bathe, Madison; Frederick J. Montgomery, Sun Prairie, both of Wis.

[73] Assignee: Ohmeda Inc., Liberty Corner, N.J.

[21] Appl. No.: 766,834

[22] Filed: Dec. 13, 1996

Related U.S. Application Data

[60] Provisional application No. 60/021,840, Jul. 10, 1996.
[51] Int. Cl.[6] .................................................. A61M 16/00
[52] U.S. Cl. ................. 128/203.12; 128/203.14
[58] Field of Search ................ 128/203.12, 203.14, 128/203.23, 203.25, 203.26, 202.22; 73/123, 92; 436/116, 117, 118

[56] References Cited

U.S. PATENT DOCUMENTS 5,111,827  5/1992  Rantala .
5,485,827  1/1996  Zapol et al. .
5,558,083  9/1996  Bathe et al. .

*Primary Examiner*—Vincent Millin
*Assistant Examiner*—Robert N. Wieland
*Attorney, Agent, or Firm*—Roger M. Rathbun; Salvatore P. Pace

[57] ABSTRACT

A system for correcting the concentration of $NO_2$ detected by an electrochemical monitor in an apparatus for administering NO to a patient for therapeutic purposes. The system determines the effective monitoring time between the point in time that the sample of NO containing gas is removed by a sample conduit from the supply conduit to the patient and the point in time that the $NO_2$ monitor actually analyzes the sample and determines the additional amount of $NO_2$ that has been formed in the time-related reaction between NO and $O_2$ in the sample conduit. Using that additional $NO_2$ calculated value, the reading of the $NO_2$ monitor is corrected to subtract that additional calculated $NO_2$ from the monitor read value to produce a corrected, more accurate reading to the user.

9 Claims, 2 Drawing Sheets

SYSTEM FOR CORRECTING $NO_2$ MONITOR

This application is based upon U.S. Provisional patent application Ser. No. 60/021,840, filed Jul. 10, 1996.

BACKGROUND

This invention relates to a system for monitoring the concentration of $NO_2$ in a gas stream that is provided to a patient during the administration of nitric oxide and, more particularly, to a system for correcting the $NO_2$ measurements that are monitored by a gas sampling system.

Nitric oxide is generally administered to patient for various therapeutic reasons, among them, the treating or preventing of bronchoconstriction or reversible pulmonary vasoconstriction. One of such treatments is the administration of NO by means of inhalation and the treatment is more fully set forth in U.S. Pat. No. 5,485,827 of The General Hospital Corporation.

The administration of NO is accomplished by various apparatus, among them is the system disclosed in U.S. Pat. No. 5,558,083 of Ohmeda Inc. In that system, an NO containing gas is provided as a gas in mixture of another gas, such as nitrogen, and the NO containing gas is mixed in a predetermined proportion with oxygen and administered to the patient.

One problem in the administration of NO with that or other methods, is that the NO reacts with oxygen to form $NO_2$ and which is a toxic substance. The reaction of NO and O2 to form $NO_2$ is time related, that is, the longer those components are in mixture, the more $NO_2$ is formed in the mixture.

Obviously, therefore, it is very important that the concentration of $NO_2$ in the gases administered to the patient be carefully monitored to insure that the level of $NO_2$ does not reach the toxic concentration to the patient. Therefore, a monitor must be used that continuously monitors the $NO_2$ level and it's equally important that such monitor provide the most accurate reading of the concentration of $NO_2$.

One of the types of monitors used for the detection of $NO_2$ is an electrochemical cell and which accurately detects the $NO_2$ concentration, however, the reading can be erroneous as an effect of the gas sampling system that takes a sample of the gas stream being administered to the patient and transmits that sample to the electrochemical monitor for analysis. As indicated, since the reaction of NO and $O_2$ is a time related reaction, the gas sampling system itself may introduce a source of error into the $NO_2$ detection system.

In the normal monitoring system, a side stream or sampling stream of gas is removed from the conduit carrying that gas stream to the patient and that side stream then conveys the sample to the $NO_2$ monitor. The difficulty arises in that the time between the actual removal of a sample of gas from the conduit to the patient and the actual analysis of the sample by the monitor allows the continuous reaction between NO and $O_2$ in that time period to increase the amount of $NO_2$ in the sample by the time the sample is actually analyzed by the monitor.

Accordingly, that level of $NO_2$ that the monitor actually detects and indicates to the user is generally a higher amount than the actual concentration of $NO_2$ in the steam of gas being administered to the patient.

SUMMARY OF THE INVENTION

In accordance with the present invention, there is provided a system for correcting the reading of a $NO_2$ monitor to account for the elapsed time from when the sample of gas is removed from the stream of gas administered to the patient to when the monitor actually analyzes the sample and provides a reading and/or signal representative of the $NO_2$ concentration.

In carrying out the invention, the system determines and takes into account the amount of time that passes between the obtaining of the sample at the sampling site and the actual analysis carried out by the monitor and uses that time to determine the additional amount of $NO_2$ that is formed by the reaction between NO and $O_2$ during that time period and thus corrects the reading of the monitor to provide a more accurate reading to the representative of the concentration of $NO_2$ in the stream of gas being administered to the patient.

DETAILED DESCRIPTION OF THE INVENTION

Figure 1:
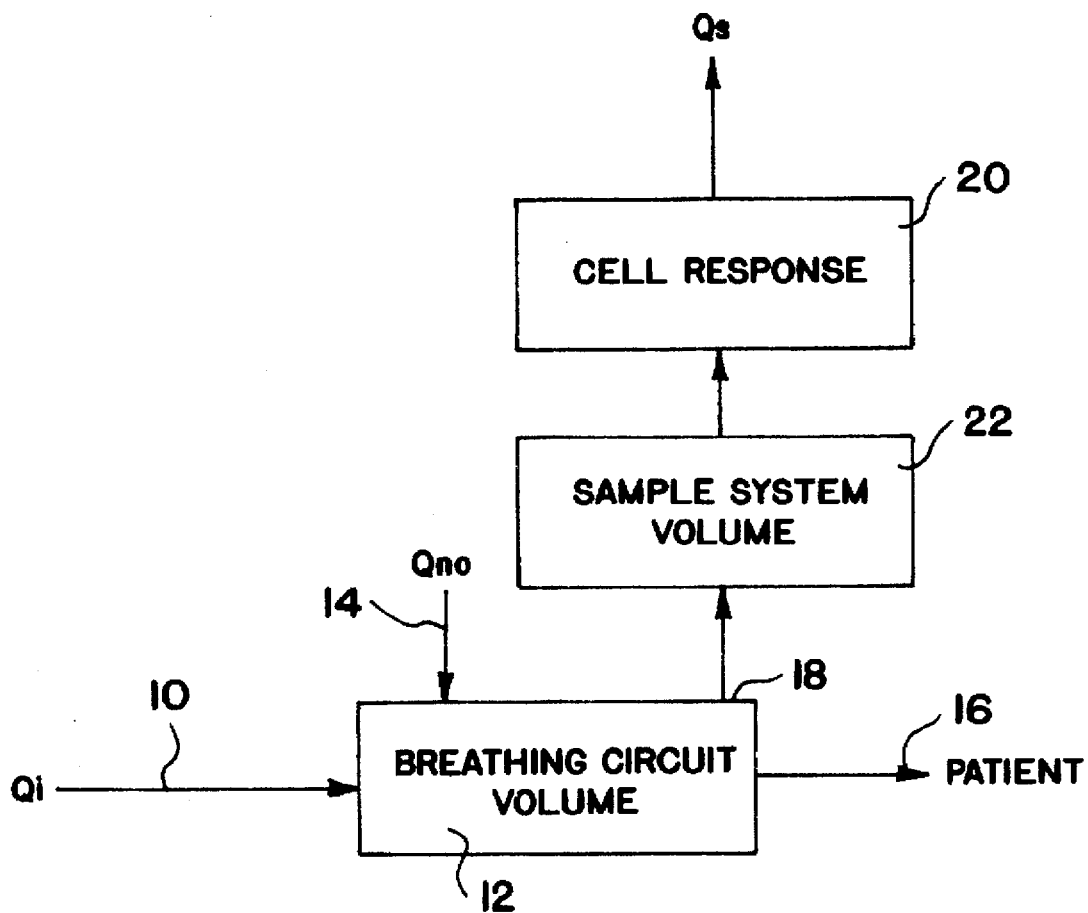
FIG. 1 is a block diagram of a typical system for side stream monitoring of gases delivered to a patient.

Turning to FIG. 1, there is shown a block diagram of a typical system for side stream monitoring of gases delivered to a patient. In FIG. 1, a portion of the system for administering NO is shown and the complete system is shown and described in U.S. Pat. No. 5,558,083 of Ohmeda Inc. As shown in FIG. 1, the stream of oxygen containing gas from the ventilator is depicted as the conduit 10 and which flow enters the breathing circuit 12. The flow of a gas containing NO is also administered to the breathing circuit 12 by means of conduit 14. As seen in the aforementioned U.S. patent, the combined stream of the oxygen containing gas from the ventilator and the gas containing NO is combined and administered to the patient 16. As stated, the reaction between the oxygen contained in the gas entering in the conduit 10 and the NO entering in the conduit 14 causes a reaction resulting in the formation of $NO_2$ which is a toxic compound.

Accordingly, it is very important to continuously monitor the concentration of $NO_2$ in the patient breathing circuit 12 relatively close to the point that the gas stream is actually introduced into the patient 16. In FIG. 1, therefore a sample point 18 is shown where a sample stream of the mixed NO containing gas is and $O_2$ containing gas is withdrawn from the breathing circuit and directed through a sample conduit to a monitor (not shown), generally of the electrochemical type, where the concentration of $NO_2$ in the sample gas is detected and a readout provided that may trigger an alarm system or otherwise provide notification to the user of the $NO_2$ concentration.

Since, however, the reaction of NO and $O_2$ to form $NO_2$ is a time related reaction, that reaction continues throughout the period from the point in time that the actual sample is taken at sample point 18 to the point in time that the monitor 20 actually determines the concentration of $NO_2$. That effective monitoring time (EMT) is determined by the flow and volume of the sample conduit and the electrochemical cell response time and is represented by the sample system volume in block 22. The electrochemical cell response time is represented by block 20.

Since $NO_2$ continues to be produced during that elapsed sampling time, the actual reading of the $NO_2$ concentration from the monitor 20 is erroneous and will read high and not give the user a true, accurate reading of the $NO_2$ concentration of the $NO_2$ in the gas stream to the patient.

It is therefore necessary to determine in some manner, the effective monitoring time from the point that the sample is withdrawn from the breathing circuit 12 at sample point 18 to the time that the monitor actually analyzes that sample to determine the $NO_2$ concentration. The effective monitoring time can be determined in a number of ways, one of which is to determine the flow in the sample conduit and to know or determine the volume in the sample conduit and the monitor response time. With those three values, the effective monitoring time of the sample between its removal from the conduit to the patient and the monitor can be readily determined.

It should be noted, however, that the $NO_2$ monitor may not be a sidestream monitor, that is, the $NO_2$ monitor may be directly receiving the sample gas from the conduit to the patient and therefore there is effectively no sample conduit and only the response time of the $NO_2$ monitor affects the production of $NO_2$. Thus, the effective monitoring time is, as will be explained, determined empirically to arrive at that time to use in the equation in determining $NO_2$ generated in the reaction of NO and $O_2$.

As an alternate method of determining the effective monitoring time, it can be determined empirically by the system shown in FIG. 1 with the use of a fast $NO_2$ sensor such as the Binos Model 1004 ultra-violet absorbance spectrometer located directly at the sample point 18 and which provides a very rapid and accurate determination of the $NO_2$ concentration at that point.

The values are thus used in the following equation to determine the effective monitoring time:

Effective Monitoring Time=$(ECMNO_2-BinosNO_2)/\{(CNO)^2 CO_2 \cdot k\}$ Where:

$ECMNO_2$ is the measurement made of the $NO_2$ by electrochemical cell (ppm);

$BinosNO_2$ is the measurement of $NO_2$ by the Binos analyzer (ppm) at the sample point 18;

CNO is the concentration of NO (ppm) of the gas in the patient breathing circuit 12; CO2 is the concentration of $O_2$ (ppm) of the gas in the patient breathing circuit 12;

k is a known constant; and

The Effective Monitoring Time (EMT) is in units of seconds.

The Binos monitor is accurate for the determination of $NO_2$ but its cost makes it prohibitive with the commercial NO administration equipment as described in the aforementioned patent. In any event, using the equation, k is a known constant and its value has been investigated and published by Sokol et al of the NICHD Neonatal Research Network, National Institute of Standards & Technology (NIST), Gaithersburg, MD and its value with the range of flows used with the NO administration equipment is about $1.27 \times 10^{-11} +/- 0.05 \times 10^{-11}$ Moles$^2$/ppm$^2$sec. and is there quantity in the equation Continuing on, a reading is taken for the $NO_2$ at the sampling point 18 with the Binos monitor and another reading is taken at the $NO_2$ monitor based on an electrochemical cell. Those readings are substituted into the prior equation to determine the sample effective monitoring time.

Thus a determination of the sample effective monitoring time can be calculated empirically for the particular system of sampling being used and that time used in a CPU to make the correction for $NO_2$ monitor being used.

Once the effective monitoring time has been determined for the particular system, the reading of the $NO_2$ concentration can be corrected by revising the equation to the following:

$CNO_2 sampling = k*(CNO)^2 * CO_2 * EMT$

By this equation, the CPU simply solves for $CNO_2$ sampling to obtain the value of $NO_2$ that is formed in the sample line during the time the sample is removed from the patient breathing circuit 12 at sample point 18 to the time that the sample is actually analyzed by the $NO_2$ monitor and a value determined for the user. Once the value of that $NO_2$ produced due to sampling is obtained, the value is simply subtracted from the actual reading of the $NO_2$ monitor that is, the electrochemical sensor, to arrive at a value that is indicative of the $NO_2$ concentration at the sample point 18, that is, the $NO_2$ concentration of the gas stream introduced to the patient 16.

Figure 2:
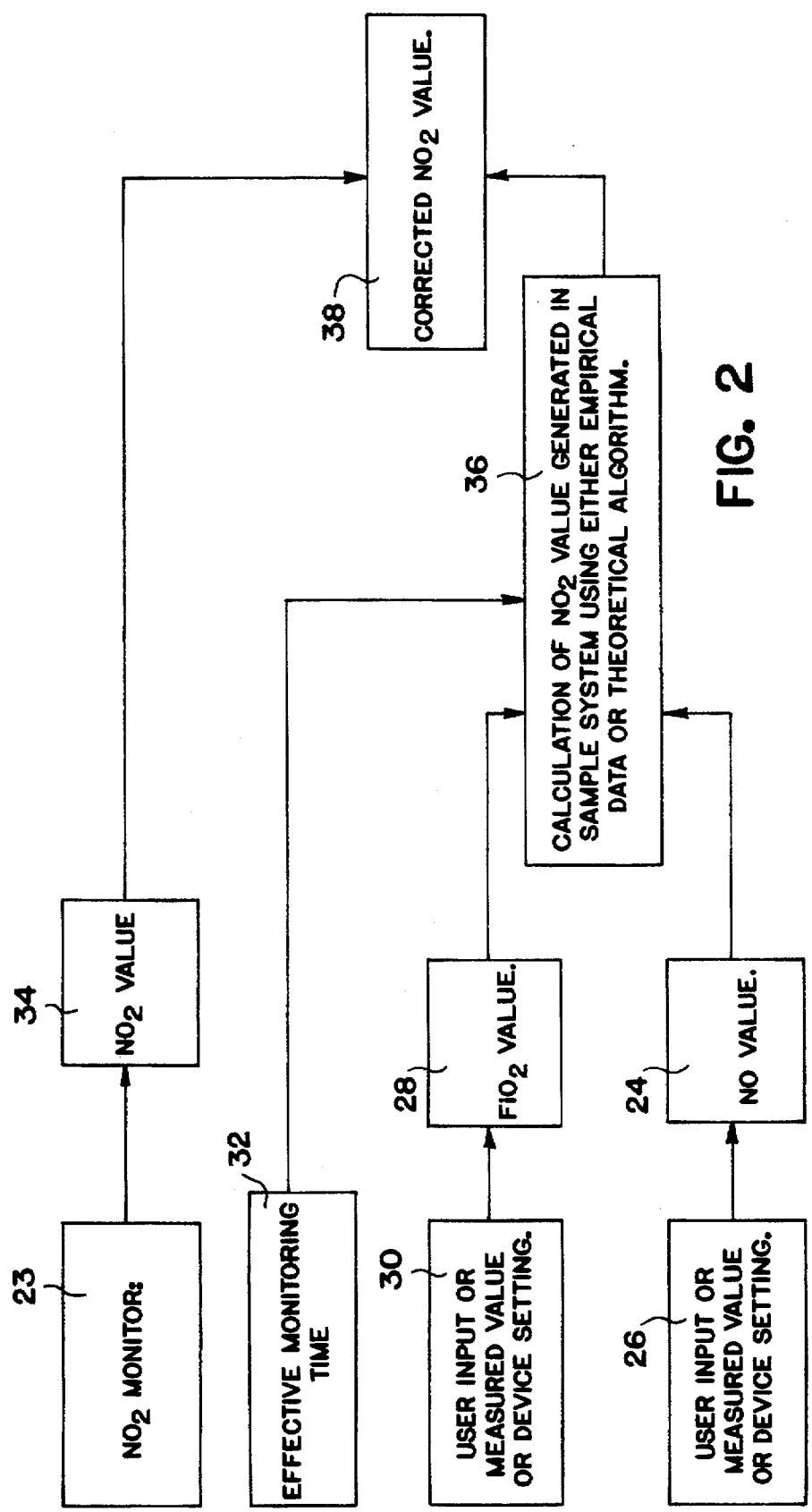
FIG. 2 is a block diagram of the steps utilized in carrying out the present invention.

Turning now to FIG. 2, there is shown a block diagram of a system for correcting the readings from the $NO_2$ monitor 23 used in the FIG. 1 embodiment. As shown, block 24 represents the value of NO that is being supplied to the patient from the overall NO administration system. The NO itself is provided by the NO supply. As noted, that supply is preferably a quantity of NO in mixture with nitrogen and typical concentrations in a gas cylinder may be in the range of 50 ppm to around 1000 ppm of NO in nitrogen. The actual value of that concentration of NO represented by block 24 may be inputted from various means depicted by block 26. Those means include a user input where a particular concentration of NO has been inputted by the user, a measured value from a NO monitor or may be a value set on the device that is providing the NO. In any event, that value of NO concentration of the gas supplied to the patient is known and represented by the block 24.

Along with that value, the value of the oxygen concentration in the stream of gas delivered to the patient, represented by block 28, is used and, again, that value may be provided by a representative block 30 as a user input value, a measured value or may be a set value of the device itself.

Basically, therefore, the blocks 24 and 28 represent the concentrations of mixed gas containing both NO and $O_2$ and the mixture itself has been mixed in the NO gas administration apparatus in accordance with the aforementioned U.S. Pat. No. 5,558,083 by combining a stream of NO containing gas and a stream of $O_2$ containing gas in a desired proportion to afford the proper and desired therapy to the patient.

As further input to the system, the sample system effective monitoring time that elapses from the point in time that the sample of the gas delivered to the patient is removed from the supply conduit to the patient and the point in time that the sample thus removed is actually analyzed by the $NO_2$ monitor 23 and a reading provided. The effective monitoring time may be determined by a measurement or calculation of the volume in the sample circuit, the flow through that circuit and the monitor response time which also may be measured or calculated. Alternatively, the determination of the effective monitoring time may be derived through the empirical testing of the particular system by means of the equations previously referred to in this specification.

In any event, the effective measurement time represented by the block 32 is the time that the $O_2$ and NO are reacting in the sample line and is used by the CPU to determine the amount of $NO_2$ generated from that reaction during the sampling of the gas to the patient.

As a further data or value to the present monitor correction system, depicted in block 34, the actual reading representative of the $NO_2$ concentration determined by the monitor having received the sample of gas from the patient circuit is used. Thus the value represented by block 34 has had the further reaction of $O_2$ and NO that has taken place during the elapsed time the sample is removed from the patient breathing circuit to the time the monitor actually makes an analysis and provides a reading of the $NO_2$ concentration.

The aforementioned values of $O_2$ concentration, NO, and effective monitoring time are fed into a CPU at block 36 where the data is processed with the aforedescribed equation to reach a value reaction of $NO_2$ created due to the reaction of NO and $O_2$ during the period of time that those constituents are together in the sample conduit. The result is a value of $NO_2$ and which is then used to correct the value of $NO_2$ detected by the $NO_2$ monitor 23 value of block 34 by subtracting the calculated value from the detected value to arrive at a corrected $NO_2$ concentration. In conventional manner, that corrected value can then be used in a display to the user and/or used to trigger an alarm condition in the event of excess $NO_2$ concentration.

Numerous further variations and combinations of the features discussed above can be utilized without departing from the spirit of the invention as defined by the claims below. Accordingly, the foregoing description of the preferred embodiment should be taken by way of illustration rather than by way of limitation of the invention as claimed.

We claim:

1. A method of correcting the readings of a $NO_2$ monitor in a system for administering a NO containing gas go to a patient and oxygen through a supply conduit, said method comprising the steps of:

(a) withdrawing from the supply conduit a sample of the NO containing gas and oxygen being delivered to a patient at a point in time, (b) transferring the sample to the $NO_2$ monitor in a sample conduit, (c) determining the concentration of $NO_2$ in the sample by means of the $NO_2$ monitor and providing a reading indicative of such concentration, (d) determining the concentration of $O_2$ and NO in the sample, (e) determining the effective time between the point of time that the sample is withdrawn in step (a) and the time the concentration of $NO_2$ is determined in the sample by the $NO_2$ monitor in step (c), (f) calculating the amount of $NO_2$ generated in the sample conduit and the $NO_2$ monitor based on the time determined in step (e) and the concentration of $O_2$ and NO determined in step (d), and (g) using the amount of $NO_2$ generated in the sample conduit and the $NO_2$ monitor as calculated in step (f) to correct the reading indicative of the concentration of $NO_2$ determined in step (c) to determine the concentration of $NO_2$ at the point the sample is withdrawn from the conduit.

2. A method of correcting the readings of a $NO_2$ monitor in a system for administering a NO containing gas to a patient by a supply conduit as defined in claim 1 wherein said step of determining the effective monitoring time comprises empirically testing of the sample conduit with a known sample of gas containing NO.

3. A method of correcting the readings of a $NO_2$ monitor in a system for administering a NO containing gas to a patient by a supply conduit as defined in claim 1 wherein said step of determining the effective monitoring time comprises calculating the time by using the flow through the sample conduit, the volume of the sample conduit and the response time of the $NO_2$ monitor.

4. A method of correcting the readings of a $NO_2$ monitor in a system for administering a NO containing gas to a patient by a supply conduit as defined in claim 1 wherein the step of calculating the amount of $NO_2$ generated in the sample conduit is includes determining the $O_2$ and NO concentrations set by the user.

5. A method of correcting the readings of a $NO_2$ monitor in a system for administering a NO containing gas to a patient by a supply conduit as defined in claim 1 wherein the step of calculating the amount of $NO_2$ generated in the sample conduit includes monitoring the values of NO and $O_2$ in the patient conduit.

6. A system for correcting the readings of a $NO_2$ monitor in a means for administering a NO containing gas and oxygen to a patient through a supply conduit, said system comprising:

a supply of a NO containing gas, a supply of a $O_2$ containing gas, means to mix said NO containing gas and said $O_2$ containing gas to a desired concentration of NO to supply said mixed gas to the patient through said supply conduit, means for removing a sample of said mixed gas from said supply conduit at a sample point at a first point of time, an $NO_2$ monitor receiving the sample of mixed gas, said $NO_2$ monitor adapted to analyze the concentration of $NO_2$ in said sample of mixed gas and to provide a signal indicative of said concentration at a second point of time, means to determine the amount of $NO_2$ generated by the reaction of NO and $O_2$ during the period between said first and second points in time, and means to correct the signal indicative of the $NO_2$ concentration from said $NO_2$ monitor by using said amount of $NO_2$ generated to provide a corrected signal indicative of the $NO_2$ concentration of $NO_2$ in the gas being delivered to the patient at said sample point.

7. A system for correcting the readings of a $NO_2$ monitor in a means for administering a NO containing gas and oxygen to a patient as defined in claim 6 wherein said means to determine the amount of $NO_2$ generated comprises means to empirically determine the time between the first and second points in time.

8. A system for correcting the readings of a $NO_2$ monitor in a means for administering a NO containing gas and oxygen to a patient as defined in claim 6 wherein said means to determine the amount of $NO_2$ generated comprises sensing the concentrations of NO and $O_2$ in said sample of mixed gases.

9. A system for correcting the readings of a $NO_2$ monitor in a means for administering a NO containing gas and oxygen to a patient as defined in claim 6 wherein said means to determine the amount of $NO_2$ generated comprises a central processing unit (CPU).

* * * * *